(12) United States Patent
Beato et al.

(10) Patent No.: US 8,309,553 B2
(45) Date of Patent: Nov. 13, 2012

(54) ANHYDROUS CRYSTAL FORM OF OVREPITANT MALEATE

(75) Inventors: Stefania Beato, Verona (IT); Franco Sartor, Verona (IT); Ian Philip Steeples, Stevenage (GB)

(73) Assignee: Glaxo Group Limited, Greenford, Middlesex (GB)

( * ) Notice: Subject to any disclaimer, the term of this patent is extended or adjusted under 35 U.S.C. 154(b) by 142 days.

(21) Appl. No.: 12/936,407

(22) PCT Filed: Apr. 9, 2009

(86) PCT No.: PCT/EP2009/054295
§ 371 (c)(1),
(2), (4) Date: Oct. 5, 2010

(87) PCT Pub. No.: WO2009/124996

PCT Pub. Date: Oct. 15, 2009

(65) Prior Publication Data
US 2011/0166150 A1 Jul. 7, 2011

(30) Foreign Application Priority Data
Apr. 11, 2008 (GB) .................................. 0806652.4

(51) Int. Cl.
*A61K 31/495* (2006.01)
(52) U.S. Cl. .................... 514/249; 544/349; 546/245
(58) Field of Classification Search .................. 514/249; 544/349; 546/245
See application file for complete search history.

(56) References Cited

FOREIGN PATENT DOCUMENTS

| WO | 03066635 A | 8/2003 |
|---|---|---|
| WO | 2007137247 A2 | 11/2007 |
| WO | 2008046882 A | 4/2008 |

OTHER PUBLICATIONS

Correa, C.; Guidelines for the examination of pharmaceuticals patents: Developing a public health perspective.; Working Paper. University of Buenos Aires. ICSTD-UNCTAD-WHO (International Centre for Trade and Sustainable development, United Nations Conference on Trade and Development, World Health Organization).; Mar. 2008.
Byrn, S.R., et al.; Polymorphs; Solid State Chemistry of Drugs; 1999; Chapter 10, pp. 143-232; Second Edition, SSCI Inc.

*Primary Examiner* — Douglas M Willis
(74) *Attorney, Agent, or Firm* — J. Scott Young

(57) ABSTRACT

The invention relates to anhydrous crystalline orvepitant maleate (Form 1), pharmaceutical formulations comprising the same, its use in therapy and processes for preparing the same, wherein orvepitant is as shown in formula (I).

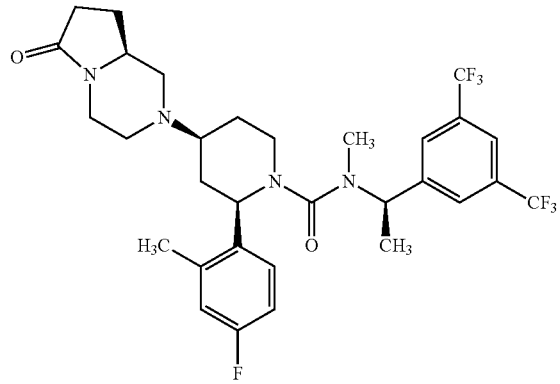

(I)

7 Claims, 5 Drawing Sheets

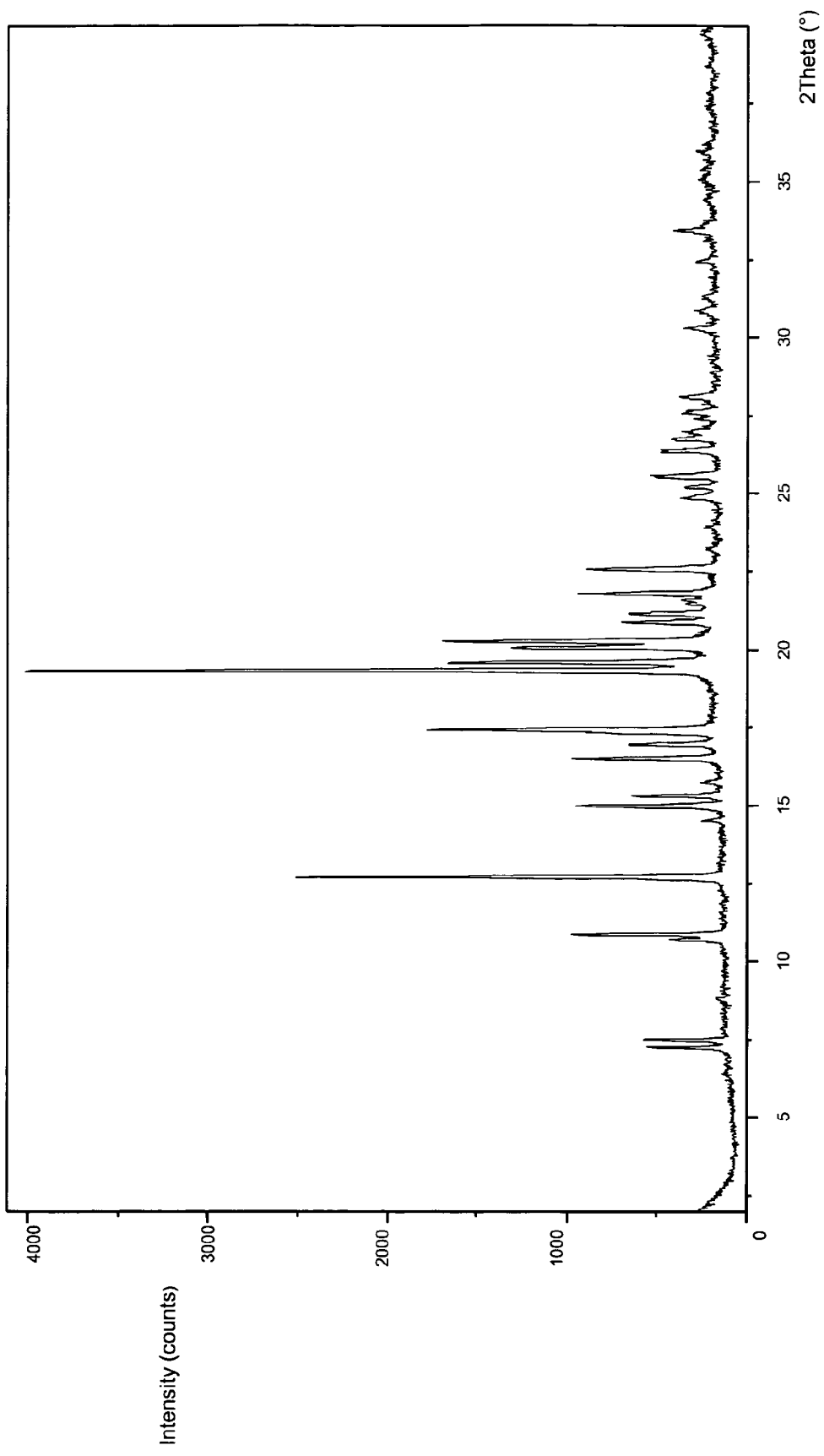
Figure 1 – XRD pattern of Orvepitant Maleate Form 1

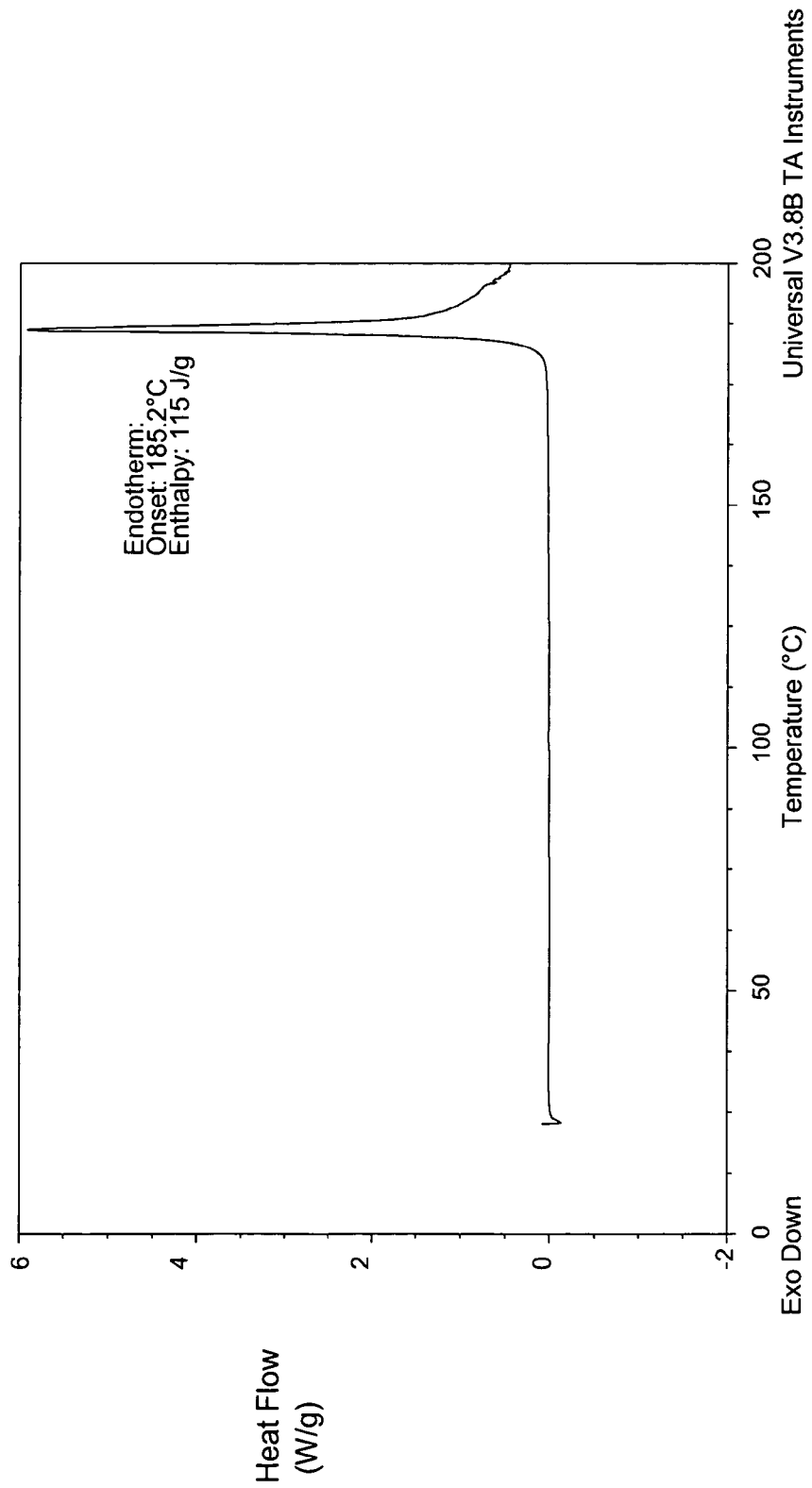
Figure 2 – DSC for Orvepitant Maleate Form 1

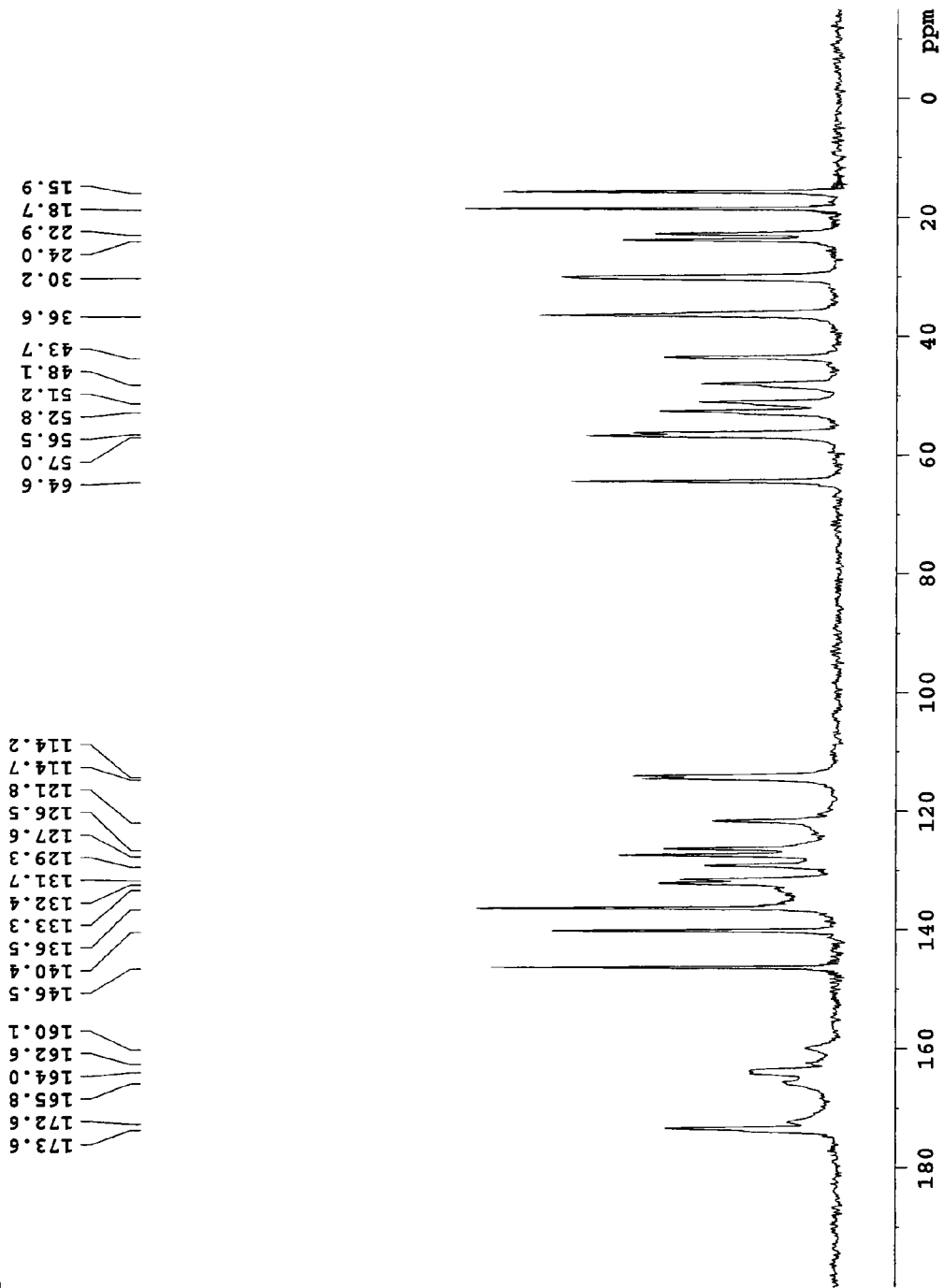
Figure 3 – NMR spectrum of Orvepitant Maleate Form 1

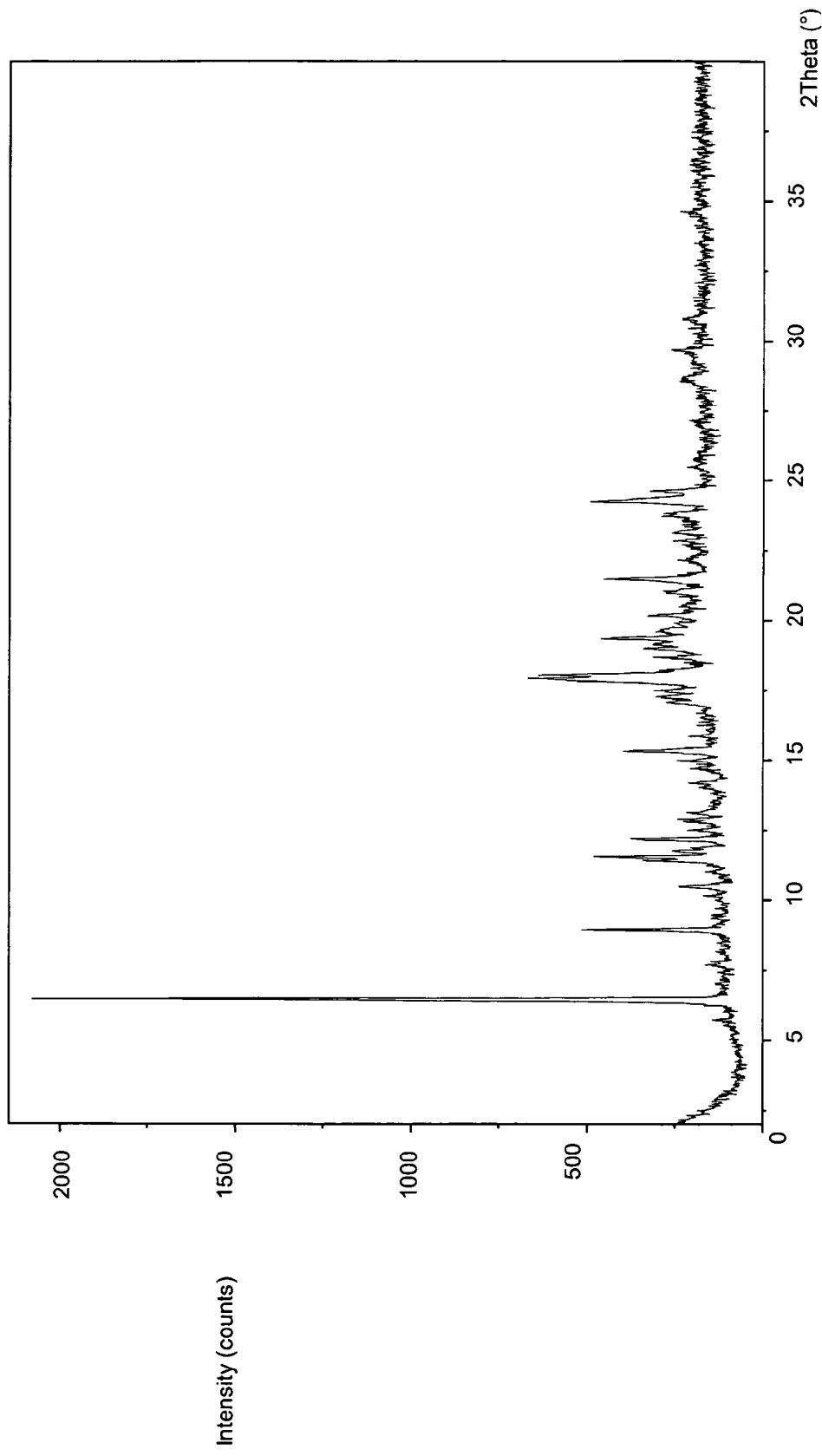
Figure 4 – XRD pattern of Orvepitant Maleate Form 2

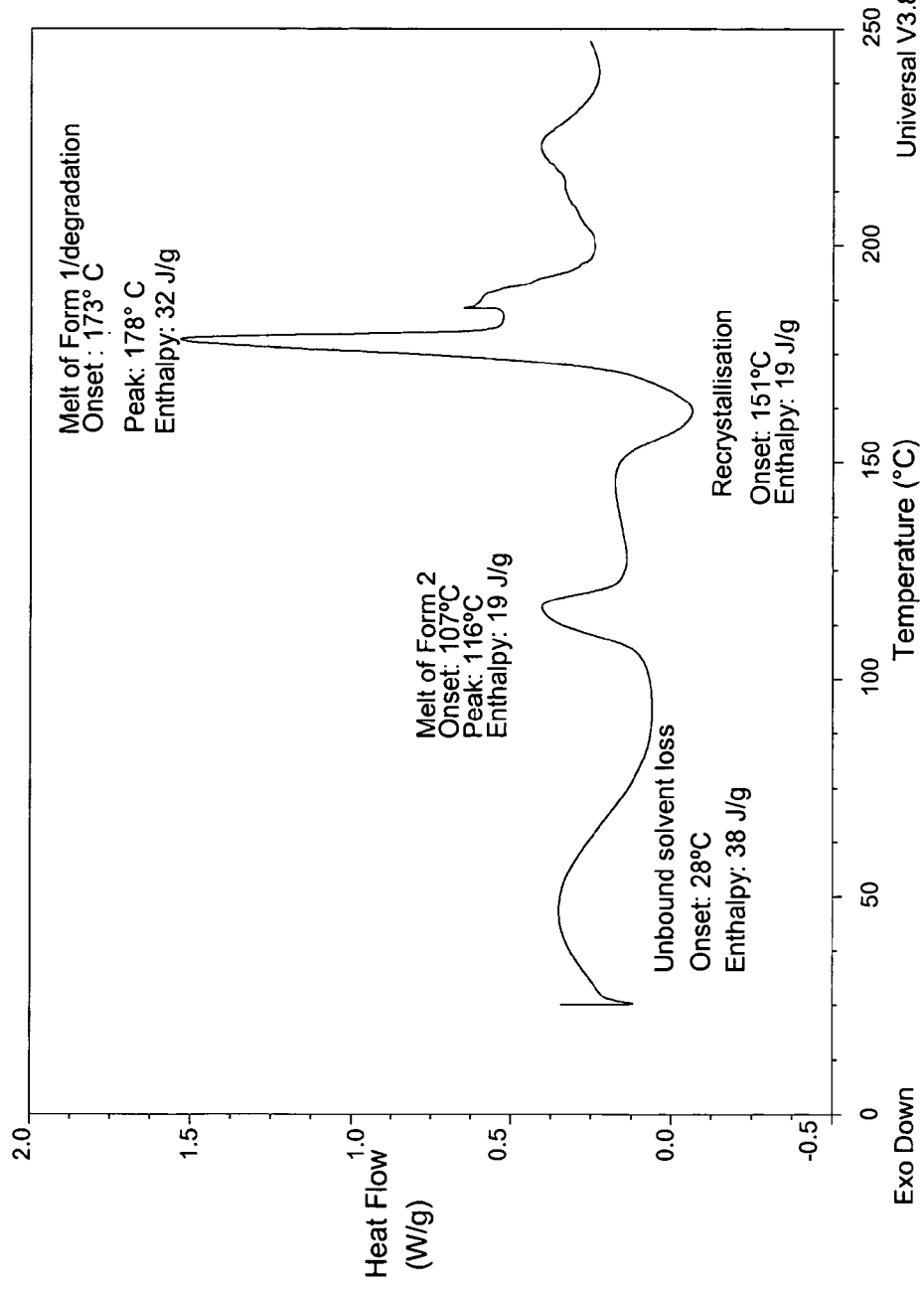
Figure 5 – DSC for Orvepitant Maleate Form 2

ANHYDROUS CRYSTAL FORM OF OVREPITANT MALEATE

CROSS-REFERENCE TO RELATED APPLICATIONS

This application is filed pursuant to 35 USC 371 as a United States National Phase Application of International Patent Application Serial No. PCT/EP2009/054295 filed on Apr. 9, 2009, which claims priority from 0806652.4 filed on Apr. 11, 2008 in the United Kingdom.

FIELD OF THE INVENTION

The present invention relates to a crystalline form of the NK1 antagonist compound orvepitant maleate, pharmaceutical formulations comprising this crystalline form, its use in therapy and processes for preparing the same.

BACKGROUND OF THE INVENTION

WO03/066635 describes a number of diazabicycle derivatives having NK1 activity, including the 2-(R)-(4-Fluoro-2-methyl-phenyl)-4-(S)-((8aS)-6-oxo-hexahydro-pyrrolo[1,2-a]-pyrazin-2-yl)piperidine-1-carboxylic acid [1-(R)-(3,5-bis-trifluoromethyl-phenyl)-ethyl]-methylamide (otherwise known as orvepitant).

The structure of the 2-(R)-(4-Fluoro-2-methyl-phenyl)-4-(S)-((8aS)-6-oxo-hexahydro-pyrrolo[1,2-a]-pyrazin-2-yl)-piperidine-1-carboxylic acid [1-(R)-(3,5-bis-trifluoromethyl-phenyl)-ethyl]-methylamide (otherwise known as orvepitant) is shown in formula (I) below:

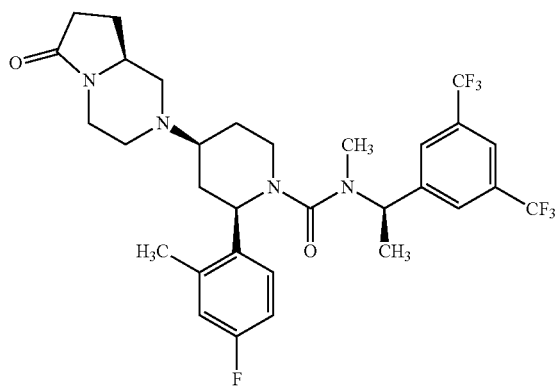

(I)

Hereinafter any reference to orvepitant refers to the compound of formula (I). Orvepitant may also be known as:
CAS Index Name
1-Piperidinecarboxamide, N-[(1R)-1-[3,5-bis(trifluoromethyl)phenyl]ethyl]-2-(4-fluoro-2-methylphenyl)-4-[(8aS)-hexahydro-6-oxopyrrolo[1,2-a]pyrazin-2(1H)-yl]-N-methyl-, (2R,4S) and
IUPAC Name:
(2R,4S)—N-{(1R)-1-[3,5-bis(trifluoromethyl)phenyl]ethyl}-2-(4-fluoro-2-methylphenyl)-N-methyl-4-[(8aS)-6-oxohexahydropyrrolo[1,2-a]pyrazin-2(1H)-yl]-1-piperidinecarboxamide.

A preferred salt of this compound is its hydrochloride salt which is otherwise known as orvepitant hydrochloride.

A further preferred salt of this compound is its maleate salt which is otherwise known as orvepitant maleate.

Particularly Example 11C of WO03/066635 describes the synthesis of orvepitant maleate using substantially the same experimental conditions described in the Example 1 in the present patent application.

We have now found that orvepitant maleate can be obtained in a new crystalline form. In particular, we have discovered a form of orvepitant maleate which is anhydrous and crystalline and which surprisingly has particularly good pharmaceutical properties. This is particularly stable and essentially non hygroscopic. It also has good storage properties and can be readily formulated into pharmaceutical compositions such as tablets and capsules.

The processes for the preparation of the anhydrous crystalline form of the present invention also show a high degree of robustness, an advantage for a highly regulated compound. Batches of this crystalline form can, by the processes of this invention, be made consistently to a high crystal form purity i.e., where the proportion of solvated and other anhydrous crystalline forms of orvepitant maleate is limited (particularly less than 10%, more particularly less than 5% and still more particularly less than 3%).

Polymorphism is defined as the ability of an element or compound to crystallise in more than one distinct crystalline phase. Thus polymorphs are distinct solids sharing the same molecular formula, however since the properties of any solid depends on its structure, different polymorphs may exhibit distinct physical properties such as different solubility profiles, different melting points, different dissolution profiles, different thermal and/or photostability, different shelf life, different suspension properties and different physiological absorption rate. Inclusion of a solvent in the crystalline solid leads to solvates, and in the case of water as a solvent, hydrates.

Polymorphic forms of a compound may be distinguished from one another and from an amorphous phase of the compound by methods including but not limited to X-ray powder diffraction (XRD), infra-red spectroscopy (IR), Raman spectroscopy, differential scanning calorimetry (DSC) and solid state nuclear magnetic resonance (ssNMR).

SUMMARY OF THE INVENTION

The present invention provides a polymorph of orvepitant maleate designated "Form 1".

Form 1 of orvepitant maleate may be characterized and differentiated using a number of conventional analytical techniques, including but not limited to X-ray powder diffraction (XRD), differential scanning calorimetry (DSC) and solid state nuclear magnetic resonance (solid state NMR).

There is thus provided in a first aspect of the invention orvepitant maleate in anhydrous crystalline form (Form 1) characterized by substantially the same X-ray powder diffraction (XRD) pattern as FIG. 1, wherein the XRD pattern is expressed in terms of 2 theta angles and obtained with a diffractometer using copper Kα X-radiation.

As a second aspect, the invention provides orvepitant maleate in anhydrous crystalline form (Form 1) characterized by substantially the same X-ray powder diffraction (XRD) pattern as FIG. 1, wherein the XRD pattern is expressed in terms of 2 theta angles and obtained with a diffractometer using copper Kα X-radiation, wherein the XRD pattern comprises 2 theta angle peaks at essentially the following positions 7.3±0.1, 7.5±0.1, 10.7±0.1, 10.9±0.1, 12.7±0.1, 15.0±0.1, 15.3±0.1, 16.5±0.1, 17.0±0.1, 17.5±0.1, 19.3±0.1, 19.6±0.1, 20.1±0.1, 20.3±0.1, 20.9±0.1, 21.1±0.1, 21.8±0.1, 22.6±0.1 degrees, which correspond respectively to d-spacings at 12.2, 11.8, 8.3, 8.1, 7.0, 5.9, 5.8, 5.4, 5.2, 5.1, 4.6, 4.5, 4.4, 4.4, 4.3, 4.2, 4.1, 3.9 Angstroms (Å).

As a third aspect, the invention provides orvepitant maleate in anhydrous crystalline form (Form 1) characterized by X-ray powder diffraction (XRD) pattern expressed in terms of 2 theta angles and obtained with a diffractometer using copper Kα X-radiation, wherein the XRD pattern comprises 2 theta angle peaks at essentially at 7.3±0.1, 7.5±0.1, 10.9±0.1, 12.7±0.1, 16.5±0.1 degrees, which correspond respectively to d-spacings at 12.2, 11.8, 8.1, 7.0 and 5.4 Angstroms (Å).

As a fourth aspect, the present invention provides orvepitant maleate in anhydrous crystalline form (Form 1) characterized by substantially the same $^{13}$C solid state nuclear magnetic resonance (solid state NMR) spectrum as FIG. 3, wherein the solid state NMR spectrum is obtained on a spectrometer operating at a frequency of 90.55 MHz for $^{13}$C observation using a 4 mm Bruker HFX MAS (magic-angle spinning) probe at a temperature of 296K, a spinning speed of 10 kHz.

As a fifth aspect, the present invention provides orvepitant maleate in anhydrous crystalline form (i.e. Form 1) characterized by a solid state NMR spectrum obtained using a spectrometer operating at a frequency of 90.55 MHz for $^{13}$C observation using a 4 mm Bruker HFX MAS (magic-angle spinning) probe at a temperature of 296K, a spinning speed of 10 kHz wherein the solid state NMR comprises chemical shifts at 173.6±0.3, 172.6±0.3, 165.8±0.3, 164.0±0.3, 162.6±0.3, 160.1±0.3, 146.5±0.3, 140.4±0.3, 136.5±0.3, 132.4±0.3, 131.7±0.3, 129.3±0.3, 127.6±0.3, 126.5±0.3, 121.8±0.3, 114.7±0.3, 114.2±0.3, 64.6±0.3, 57.0±0.3, 56.5±0.3, 52.8±0.3, 51.2±0.3, 48.1±0.3, 43.7±0.3, 36.6±0.3, 30.2±0.3, 24.0±0.3, 22.9±0.3, 18.7±0.3, 15.9±0.3 ppm.

As another aspect, the present invention provides a pharmaceutical composition comprising anhydrous crystalline orvepitant maleate (i.e. Form 1) according to the present invention. The pharmaceutical composition may further comprise one or more pharmaceutically acceptable carriers or diluents.

As another aspect, the present invention provides a method for the treatment or prophylaxis of Central Nervous System disorders comprising administering to the mammal, an effective amount of anhydrous crystalline orvepitant maleate (Form 1) according to the present invention.

As another aspect, the present invention provides a method for the treatment or prophylaxis of depression, anxiety, post-traumatic stress disorders, emesis and/or sleep disorders.

As another aspect, the present invention provides anhydrous crystalline orvepitant maleate (Form 1) according to the present invention for use in therapy.

As another aspect, the present invention provides the use of anhydrous crystalline orvepitant maleate (Form 1) according to the present invention in the preparation of a medicament for the treatment or prophylaxis of Central Nervous System diseases.

As another aspect, the present invention provides the use of anhydrous crystalline orvepitant maleate (Form 1) according to the present invention in the preparation of a medicament for the treatment or prophylaxis of depression, anxiety, posttraumatic stress disorders, emesis and/or sleep disorders.

As another aspect, the present invention provides a process for preparing anhydrous crystalline orvepitant maleate (Form 1).

In one particular embodiment, the process comprises the step of:

a) forming orvepitant in solution either in free base or salt form;
b) converting said free base orvepitant or a salt thereof (when not the maleate salt) to orvepitant maleate;
c) isolating orvepitant maleate from the solution leaving orvepitant maleate in a anhydrous form (i.e. Form 2) or orvepitant maleate solvated forms or a mixture thereof;
d) treating orvepitant maleate from step c with a solubilising solvent or mixture of solvents
e) heating the mixture and adding seeds of orvepitant maleate Form 1 to convert an amount of the orvepitant maleate from step c) into Form 1 orvepitant maleate and
f) cooling and isolating said anhydrous crystalline Form 1.

In a further embodiment, the process comprises the step of:

a) forming orvepitant in solution either in free base or salt form;
b) converting said free base orvepitant or a salt thereof (when not the maleate salt) to orvepitant maleate;
c) isolating orvepitant maleate from the solution leaving orvepitant maleate in anhydrous form (i.e. Form 2) or orvepitant maleate solvated forms or a mixture thereof;
d) slurrying orvepitant maleate Form 2 or orvepitant maleate solvated forms or a mixture thereof in a hydrocarbon solvent at a temperature of about ambient temperature to about the boiling point of the solvent for a period of time to convert the orvepitant maleate Form 2 or orvepitant maleate solvated forms or a mixture thereof to Form 1 orvepitant maleate.
e) cooling and isolating said anhydrous crystalline Form 1.

BRIEF DESCRIPTION OF THE DRAWINGS

FIG. 1. The XRD pattern of Form 1 orvepitant maleate according to the present invention. The XRD pattern is expressed in terms of 2 theta angles and obtained with a diffractometer using copper Kα X-radiation, according to the procedures described herein.

FIG. 2. The differential scanning calorimetry (DSC) thermogram for Form 1 orvepitant maleate according to the present invention. The DSC was carried out on a TA Q1000 TA system at a scan rate of 10° C. per minute, using a sample size of between 1 and 2 mg according to the procedures described herein.

FIG. 3. The solid state NMR spectrum of Form 1 orvepitant maleate according to the present invention. The solid state NMR spectrum was obtained on a spectrometer operating at a frequency of 90.55 MHz for $^{13}$C observation at a temperature of 296K, a spinning speed of 10 kHz, according to the procedures described herein.

FIG. 4. The XRD pattern of Form 2 orvepitant maleate. The XRD pattern is expressed in terms of 2 theta angles and obtained with a diffractometer using copper Kα X-radiation, according to the procedures described herein.

FIG. 5. The differential scanning calorimetry (DSC) thermogram for Form 2 orvepitant maleate. The DSC was carried out on a TA Q1000 TA system at a scan rate of 10° C. per minute, using a sample size of between 1 and 2 mg according to the procedures described herein.

DETAILED DESCRIPTION OF THE INVENTION

The present invention provides a crystalline form of orvepitant maleate (Form 1) exhibiting one or more advantageous pharmaceutical properties or other advantages over other polymorphic forms or over an amorphous phase. This Form 1 is particularly stable and essentially non hygroscopic. It also has good storage properties and can be readily formulated into pharmaceutical compositions such as tablets and capsules. The crystalline form of the present invention is thermodynamically more stable than, for example, Form 2.

"Form 1 orvepitant maleate" as used herein refers to any of: 1) an anhydrous crystalline form of orvepitant maleate having substantially the same XRD pattern as shown in FIG. 1 when measured with a properly aligned diffractometer copper Kα X-radiation; 2) an anhydrous crystalline form of orvepitant maleate having substantially the thermogram as shown in FIG. 2 when the differential scanning calorimetry (DSC) thermogram was carried out on a TA Q1000 calorimeter. at a scan rate of 10° C. per minute, using a sample size of between 1 and 2 mg weighed into an aluminium pan, a pan lid placed on top and lightly crimped without sealing the pan, or 3) an anhydrous crystalline form of orvepitant maleate having substantially the same solid state NMR spectra as shown in FIG. 3, obtained on a spectrometer operating at a frequency of 90.55 MHz for $^{13}C$ observation at a temperature of 296K, a spinning speed of 10 kHz.

The X-ray powder diffraction (XRD) pattern of Form 1 orvepitant maleate can be determined using conventional techniques and equipment known to those skilled in the art of analytical chemistry and physical characterization. The diffraction pattern of FIG. 1 was obtained with a PANalytical X'-Pert Pro powder diffractometer model PW3040/60 equipped with an X'Celerator detector using copper Kα X-radiation The acquisition conditions were: generator tension: 40 kV, generator current: 45 mA, start angle: 2.0° 2 theta, end angle: 40.0° 2 theta, step size: 0.0167° 2 theta, time per step: 31.75 seconds. The sample was prepared by mounting a few milligrams of sample on a silicon wafer (zero background) plate, resulting in a thin layer of powder.

A powder sample of Form 1 orvepitant maleate obtained from Example 5 was used to produce the XRD pattern of FIG. 1. 2 Theta angles in degrees x-axis) are plotted against peak intensity in terms of the count rate per seconds (y-axis). The XRD pattern is unique to the particular form; exhibiting a unique set of diffraction peaks which can be expressed in 2 theta angles (°) or d-spacings (Å).

2 Theta diffraction angles and corresponding d-spacing values account for positions of various peaks in the XRD pattern, d-spacing values are calculated with observed 2 theta angles and copper Kα1 wavelength using the Bragg equation. Slight variations in observed 2 theta angles and d-spacings are expected based on the specific diffractometer employed and the analyst's sample preparation technique. More variation is expected for the relative peak intensities. Large variations of relative peak intensities may be observed due to preferred orientation resulting from differences in crystal morphology. Variations in observed 2 theta angles and d-spacings may also be observed depending on the temperature at which the values are measured. Identification of the exact crystal form of a compound should be based primarily on observed 2 theta angles or d-spacings.

To identify Form 1, certain characteristic 2 theta angles occur at 7.3±0.1, 7.5±0.1, 10.9±0.1, 12.7±0.1, 16.5±0.1 degrees, which correspond respectively to d-spacings at 12.2, 11.8, 8.1, 7.0 and 5.4 Angstroms (Å).

Although one skilled in the art can identify Form 1 from these characteristic 2 theta angle peaks or d-spacings, in some circumstances it may be desirable to rely upon additional 2 theta angles or d-spacings for the identification of Form 1 compound of Formula (I).

Thus, Form 1 orvepitant maleate typically exhibits 2 theta angle peaks at essentially the following positions 7.3±0.1, 7.5±0.1, 10.7±0.1, 10.9±0.1, 12.7±0.1, 15.0±0.1, 15.3±0.1, 16.5±0.1, 17.0±0.1, 17.5±0.1, 19.3±0.1, 19.6±0.1, 20.1±0.1, 20.3±0.1, 20.9±0.1, 21.1±0.1, 21.8±0.1, 22.6±0.1 degrees, which correspond respectively to d-spacings 12.2, 11.8, 8.3, 8.1, 7.0, 5.9, 5.8, 5.4, 5.2, 5.1, 4.6, 4.5, 4.4, 4.4, 4.3, 4.2, 4.1, 3.9 Angstroms (Å).

Some margin of error is present in each of the 2 theta angle assignments and d-spacings reported above. The error in determining d-spacings decreases with increasing diffraction scan angle or decreasing d-spacing. The margin of error in the foregoing 2 theta angles is approximately ±0.1 degrees for each of the foregoing peak assignments.

Since some margin of error is possible in the assignment of 2 theta angles and d-spacings, the preferred method of comparing XRD patterns in order to identify the particular form of a sample of orvepitant maleate is to overlay the XRD pattern of the unknown sample over the XRD pattern of a known form. For example, one skilled in the art can overlay an XRD pattern of an unknown sample of orvepitant maleate, obtained using the methods described herein, over FIG. 1 and, using expertise and knowledge in the art, readily determine whether the XRD pattern of the unknown sample is substantially the same as the XRD pattern of Form 1 orvepitant maleate.

Considering 2 theta angles (°) and d-spacing (Å), Form 1 orvepitant maleate exhibits the following XRD pattern characteristics:

| Form 1 orvepitant maleate | |
|---|---|
| 2 theta angle (°)[1] | Å |
| 7.3 | 12.2 |
| 7.5 | 11.8 |
| 10.7 | 8.3 |
| 10.9 | 8.1 |
| 12.7 | 7.0 |
| 15.0 | 5.9 |
| 15.3 | 5.8 |
| 16.5 | 5.4 |
| 17.0 | 5.2 |
| 17.5 | 5.1 |
| 19.3 | 4.6 |
| 19.6 | 4.5 |
| 20.1 | 4.4 |
| 20.3 | 4.4 |
| 20.9 | 4.3 |
| 21.1 | 4.2 |
| 21.8 | 4.1 |
| 22.6 | 3.9 |

[1]Margin of error = approx. ±0.1 degrees.

Based upon the foregoing characteristic features of the XRD pattern of Form 1 orvepitant maleate, one skilled in the art can readily identify Form 1 orvepitant maleate. It will be appreciated by those skilled in the art that the XRD pattern of a sample of Form 1 orvepitant maleate, obtained using the methods described herein, may exhibit additional peaks. The foregoing table provides the most intense peaks which are characteristic of that particular crystalline form. This table does not represent an exhaustive list of peaks exhibited by Form 1 orvepitant maleate.

The X-ray powder diffraction (XRD) pattern of Examples 2, 3, 4, 6, 7 and 8 are consistent with that reported in FIG. 1.

Solid state nuclear magnetic resonance (solid state NMR) is another conventional analytical technique for identifying the physical characteristics of a sample of Form 1 orvepitant maleate. The solid state NMR spectra of Form 1 orvepitant maleate is unique. The solid state NMR spectrum of the anhydrous crystalline form of Form 1 orvepitant maleate, according to the present invention, is determined using conventional equipment and techniques known to those skilled in the art of analytical chemistry and physical characterization.

$^{13}$C solid-state NMR data of FIG. 3 was acquired using a Bruker AV360 spectrometer operating at 90.55 MHz for $^{13}$C observation. A 4 mm Bruker HFX MAS (magic-angle spinning) probe was used. The sample was gently packed into a zirconia rotor and spun at 10 kHz, at a temperature of 296K. Data was obtained using ramped cross-polarization and a TOSS (total sideband suppression) pulse sequence. Proton decoupling was performed at an RF power of 100 kHz using the SPINAL64 decoupling sequence. Characteristic $^{13}$C NMR peak positions are reported in parts per million (ppm) frequency relative to tetramethylsilane at 0 ppm, and have a precision of +/−0.3 ppm caused by instrumental variability and calibration.

Certain characteristic chemical shifts observed in the solid state NMR spectrum of Form 1 orvepitant maleate using a spectrometer operating at a frequency of 90.55 MHz for $^{13}$C observation at a temperature of 296K, a spinning speed 10 kHz include the following: 173.6±0.3, 172.6±0.3, 165.8±0.3, 164.0±0.3, 162.6±0.3, 160.1±0.3 146.5±0.3 140.4±0.3, 136.5±0.3, 132.4±0.3, 131.7±0.3, 129.3±0.3, 127.6±0.3, 126.5±0.3, 121.8±0.3, 114.7±0.3, 114.2±0.3, 64.6±0.3, 57.0±0.3, 56.5±0.3, 52.8±0.3, 51.2±0.3, 48.1±0.3, 43.7±0.3, 36.6±0.3, 30.2±0.3, 24.0±0.3, 22.9±0.3, 18.7±0.3, 15.9±0.3 ppm.

Slight variations in observed chemical shifts are expected based on the specific spectrometer employed and the analyst's sample preparation technique. Some margin of error is present in each of the chemical shifts reported above. The margin of error in the foregoing chemical shifts is approximately ±0.3 ppm.

Since some margin of error is possible in the assignment of chemical shifts, the preferred method of determining whether an unknown form of orvepitant maleate is Form 1 orvepitant maleate is to overlay the solid state NMR spectrum of the sample over the solid state NMR spectrum provided in FIG. 3. One skilled in the art can overlay an NMR spectrum of an unknown sample of orvepitant maleate, obtained using the methods described herein, over FIG. 3 and, using expertise and knowledge in the art, readily determine whether the NMR spectrum of the unknown sample is substantially the same as the NMR spectrum of Form 1 orvepitant maleate. Specifically $^{13}$C solid state NMR data of FIG. 3 corresponds to sample of Example 8 of the present patent application.

$^{13}$C solid state NMR data was also obtained for Example 7 and it was consistent with that of FIG. 3.

Any of the foregoing analytical techniques can be used alone or in combination to identify Form 1 orvepitant maleate. In addition, other methods of physical characterization can also be employed to identify and characterize Form 1 orvepitant maleate. Examples of suitable techniques which are known to those skilled in the art to be useful for the physical characterization or identification of a crystalline anhydrous form or solvated form include but are not limited to differential scanning calorimetry and infra-red spectroscopy. These techniques may be employed alone or in combination with other techniques to characterize a sample of an unknown form of orvepitant maleate.

In another aspect, the present invention provides pharmaceutical compositions comprising Form 1 orvepitant maleate. Such pharmaceutical compositions may include one or more pharmaceutically acceptable carriers or diluents. Examples of suitable pharmaceutical compositions and methods for their preparation are described in a PCT Publication No. WO03/066635, the subject matter of which is incorporated herein by reference in its entirety. Conveniently, suitable pharmaceutical compositions can be prepared using conventional techniques, and when employed, carriers and diluents. Pharmaceutical compositions for oral administration, such as tablet and capsule formulations, are preferred.

In a further aspect, the present invention provides a process for preparing Form 1 orvepitant maleate.

Orvepitant maleate can be prepared according to the method described in PCT Publication No. WO03/066635 and PCT Publication No. WO07/048,642, the subject matter of which are incorporated herein by reference in their entirety.

The synthesis of orvepitant maleate generally leads to the formation of the compound in solution in the reaction mixture from which it may be separated and purified as a solid product.

Certain factors influence which anhydrous crystal form results. These factors include, but are not limited to nucleation, seeding (both active and inadvertant) and solvent mediated effects. The solvent composition and solvent to product ratio is critical for the nucleation of the desired form. Typically seeding can influence the nucleation of the desired form from the solvent mixture. In the following methods, conditions of separation and further processing are selected to produce Form 1 orvepitant maleate.

In one particular embodiment the process comprises the step of:
a) forming orvepitant in solution either in free base or salt form;
b) converting said free base orvepitant or a salt thereof (when not the maleate salt) to orvepitant maleate;
c) isolating orvepitant maleate from the solution leaving orvepitant maleate in a anhydrous form (i.e. Form 2) or orvepitant maleate solvated forms or a mixture thereof;
d) treating orvepitant maleate from step c with a solubilising solvent or mixture of solvents
e) heating the mixture and adding seeds of orvepitant maleate Form 1 to convert an amount of the orvepitant maleate from step c) into Form 1 orvepitant maleate and
f) cooling and isolating said anhydrous crystalline Form 1.

According to the above steps a) and b) orvepitant maleate can be formed in solution for example in iso-propanol and then it is isolated by precipitation for example by addition of iso-octane in the presence of seeds (i.e. orvepitant maleate Form 2 or orvepitant maleate solvated forms or a mixture thereof).

The orvepitant maleate Form 2 or orvepitant maleate solvated forms or a mixture thereof), can be then be separated at this stage by filtration and can then optionally be dried (step c).

Step d) can be carried out, mixing orvepitant maleate obtained from step c) with an amount of a lower ketone such as methyl isobutyl ketone in an amount of about, 100 g/L to 200 g/L, and heated for example from about 70-75° C. until the material is dissolved.

Finally, (step f) the Form 1 orvepitant maleate may be isolated by filtration after crystallisation following addition of iso-octane in an amount of about 100 g/L solvent to 200 g/L, seeding with Form 1 orvepitant maleate (step e) and cooling in the range of temperature between 25°-7° C. Optionally, the Form 1 orvepitant maleate thus produced may be dried under vacuum to remove residual solvent, for example at about 45-55° C.

Alternatively Step d) can be carried out mixing orvepitant maleate obtained from step c) with iso-propanol and heating this solution from about 50°-60° C.

In a further embodiment, the process comprises the step of:
a) forming orvepitant in solution either in free base or salt form;

b) converting said free base orvepitant or a salt thereof (when not the maleate salt) to orvepitant maleate;
c) isolating orvepitant maleate from the solution leaving orvepitant maleate in anhydrous form (i.e. Form 2) or orvepitant maleate solvated forms or a mixture thereof;
d) slurrying orvepitant maleate Form 2 or orvepitant maleate solvated forms or a mixture thereof in a hydrocarbon solvent at a temperature of about ambient temperature to about the boiling point of the solvent for a period of time to convert the orvepitant maleate Form 2 or orvepitant maleate solvated forms or a mixture thereof to Form 1 orvepitant maleate.
e) cooling and isolating said anhydrous crystalline Form 1.

The slurrying step (Step d) can be carried out in an hydrocarbon solvent such as iso-octane at temperatures ranging from about ambient to reflux temperature such as 98-99° C. for a period of time sufficient to convert orvepitant maleate Form 2 or orvepitant maleate solvated forms or a mixture thereof to Form 1 orvepitant maleate which can be collected by filtration after cooling to room temperature. Optionally, the Form 1 orvepitant maleate thus produced may be dried under vacuum to remove residual solvent, for example at about 45-55° C.

Form 1 orvepitant maleate for use in the present invention may be used in combination with other therapeutic agents. Similarly, the pharmaceutical formulations of the present invention may include one or more additional therapeutic agents. The various therapeutic agents disclosed in PCT Publication no. WO03/066635, the subject matter of which is incorporated herein by reference in its entirety, that may be combined with Form 1 orvepitant maleate are similarly applicable to Form 1 orvepitant maleate.

The invention thus provides in a further aspect the use of a combination comprising Form 1 orvepitant maleate with a further therapeutic agent in the treatment of Central Nervous System diseases (CNS).

When the Form 1 orvepitant maleate is used in combination with other therapeutic agents, the compounds may be administered either sequentially or simultaneously by any convenient route.

When combined in the same formulation it will be appreciated that the two compounds must be stable and compatible with each other and with the other components of the formulation and may be formulated for administration. When formulated separately they may be provided in any convenient formulation, in such a manner as is known for such compounds in the art.

When Form 1 orvepitant maleate is used in combination with a second therapeutic agent, the dose of each compound may differ from that when the compounds are used alone. Appropriate doses will be readily appreciated by those skilled in the art.

Form 1 orvepitant maleate and pharmaceutical compositions comprising the same are useful in therapy, particularly in the treatment of CNS disorders and psychotic disorders, in an animal, e.g. a mammal such as a human. The various therapeutic uses disclosed in PCT Publication no. WO03/066635, the subject matter of which is incorporated herein by reference in its entirety, are similarly applicable to Form 1 orvepitant maleate. Form 1 orvepitant maleate is especially useful for the treatment or prophylaxis of anxiety, depression, sleep disorders and emesis.

The present invention also provides a method for the treatment or prophylaxis of CNS disorders and psychotic disorders, in particular in the treatment or prevention of depressive states and/or in the treatment of anxiety in an animal such as a mammal (e.g., a human), which comprises administering to the animal an effective amount of Form 1 orvepitant maleate. The foregoing method is particularly useful for the treatment or prophylaxis of anxiety, depression, posttraumatic stress disorders, sleep disorders and emesis.

The present invention also provides the use of Form 1 orvepitant maleate in the preparation of a medicament for the treatment or prophylaxis of CNS disorders in an animal such as a mammal (e.g., a human), particularly for the treatment or prophylaxis of anxiety, depression, posttraumatic stress disorders, sleep disorders and emesis.

The following examples are intended for illustration only and are not intended to limit the scope of the invention in any way.

In the procedures that follow, after each starting material, reference to a description is typically provided. This is provided merely for assistance to the skilled chemist. The starting material may not necessarily have been prepared from the batch referred to.

In the Examples unless otherwise stated:
$^1$H nuclear magnetic resonance (NMR) spectra were recorded on Bruker instruments at 400 or 700 MHz, chemical shifts are reported in ppm (δ) using the residual solvent line or tetramethylsilane as internal standard. Splitting patterns are designed as s, singlet; d, double; t, triple; q, quartet; m, multiplet; b, broad. Differential scanning calorimetry (DSC) was carried out on a TA Q1000 calorimeter. Scan rate of 10° C. per minute. Sample size of between 1 and 2 mg.

The following abbreviation are used in the text:
IPA for iso-propanol; min for minutes; MIBK for methyl iso-butyl ketone; NMR for Nuclear Magnetic Resonance; ppm for parts per million; XRD for X-ray powder diffraction; w/w for weight/weight; ml for millilitres; g for grams; ca for circa; kg for kilograms.

EXAMPLE 1

Preparation of Orvepitant Maleate (Form 2)

{(1R)-1-[3,5-bis(trifluoromethyl)phenyl]ethyl}methylamine-(2R)-2-hydroxybutanedioic acid (1.8 kg) was added to ethyl acetate (5.4 litres) and 15% w/w sodium carbonate solution (5.4 litres) and was stirred until all solids had dissolved. The organic phase was separated and was washed with water (5.4 litres). Fresh ethyl acetate (6.7 litres) was added and the solution was distilled to 5.4 litres under reduced pressure. The solution was diluted with ethyl acetate (3.6 litres). The reactor was purged with carbon dioxide and a continuous steady stream of carbon dioxide was maintained. Triethylamine (810 ml) was added over 30 minutes and was rinsed in with ethyl acetate (250 ml). The reaction mixture was stirred for 30 minutes. Chlorotrimethylsilane (850 ml) was added over 30 minutes with cooling to keep the temperature between 17° C. and 23° C. and was rinsed in with ethyl acetate (250 ml). The reaction mixture was stirred for 30 minutes. Pyridine (720 ml) was added and was rinsed in with ethyl acetate (250 ml). Thionyl chloride (480 ml) was added over 10 minutes and then a rinse of ethyl acetate (500 ml). The reaction mixture was stirred at 20° C. for 16 hours under a carbon dioxide atmosphere. 28% w/w Racemic malic acid solution (5.3 litres) was added and the mixture was stirred for 15 minutes. The organic phase was separated, diluted with ethyl acetate (1.5 litres) and was washed with water (2×2.7 litres) and 20% w/w dibasic potassium phosphate solution (5.6 litres). The solution was distilled under reduced pressure to a total volume of 2.5 litres. Ethyl acetate (5 litres) was added and the solution was re-distilled to 3 litres to give a solution of {(1R)-1-[3,5-bis(trifluoromethyl)phenyl]ethyl}methylcarbamic chloride.

(2R)-2-(4-fluoro-2-methylphenyl)-4-piperidinone-(2S)-hydroxy(phenyl)ethanoic acid (1.2 kg) was added to 15% w/w sodium carbonate solution (4.8 litres) and ethyl acetate (4.8 litres) and the mixture was stirred until solids dissolved. The organic phase was separated and was washed with 20% w/w sodium chloride solution (4 litres). Fresh ethyl acetate (4.8 litres) was added and the solution of (2R)-2-(4-fluoro-2-methylphenyl)-4-piperidinone was distilled under reduced pressure to a volume of 3 litres.

The solution of (2R)-2-(4-fluoro-2-methylphenyl)-4-piperidinone was charged to the solution of {(1R)-1-[3,5-bis(trifluoromethyl)phenyl]ethyl}methylcarbamic chloride followed by an ethyl acetate (300 ml) rinse. Triethylamine (857 g) was added followed by ethyl acetate (300 ml) and the mixture was boiled at reflux for 18 hours. The slurry was cooled to 20° C. and N-acetylpiperazine (240 g) was added. The reaction mixture was stirred for 30 minutes at 20° C. and was then charged with 28% w/w racemic malic acid solution (3.6 litres). The organic phase was separated and was washed with 20% w/w sodium chloride solution (4.8 litres). Ethyl acetate (4.8 litres) was added and the solution of (2R)—N-{(1R)-1-[3,5-bis(trifluoromethyl)phenyl]ethyl}-2-(4-fluoro-2-methylphenyl)-N-methyl-4-oxo-1-piperidinecarboxamide was distilled under reduced pressure distillation to a total volume of 3 litres.

(8aS)-hexahydropyrrolo[1,2-a]pyrazin-6(2H)-one-(2S)-(acetyloxy)(phenyl)ethanoic acid (1.5 kg) was added to acetonitrile (11.4 litres) and triethylamine (450 g) was added. An acetonitrile (250 ml) rinse was added and the slurry was stirred at 20° C. for 30 min. Sodium triacetoxyborohydride (900 g) was added and the reaction was cooled to 10° C. Formic acid (396 ml) was added to the mixture over 30 min, maintaining the temperature below 15° C. An acetonitrile (250 ml) rinse was added and the reaction was warmed to 20° C. The solution of (2R)—N-{(1R)-1-[3,5-bis(trifluoromethyl)phenyl]ethyl}-2-(4-fluoro-2-methylphenyl)-N-methyl-4-oxo-1-piperidinecarboxamide in ethyl acetate was added to the reaction mixture and was rinsed in with acetonitrile (1 litre). The reaction was stirred for 16 hours at 20° C.

The slurry was distilled to 5 litres under reduced pressure. The mixture was diluted with ethyl acetate (10 litres) and was washed with 13% w/w ammonia solution (2×4 litres), and 10% w/w sodium chloride solution (4 litres). The organic solution was distilled to 5 litres under reduced pressure. The solution was diluted with IPA (8 litres) and was distilled under reduced pressure to 5 litres. Further IPA (8 litres) was added and the solution was again distilled to 5 litres.

A solution of maleic acid (248.5 g) in IPA (2.5 litres) was added. The mixture was then seeded with orvepitant maleate A (1 g) and the mixture was aged for 1 hour. Iso-octane (10 litres) was added over 30 min. and the mixture further aged for 1 hour. The slurry was cooled to 7° C. and was further aged for 90 minutes. The solid formed was filtered and washed with a 1:1 mixture of IPA/iso-octane (2×3 litres). The resulting solid was dried at 40° C. under reduced pressure to give the title compound (1.095 kg, 44%).

NMR (CD$_3$OD) δ (ppm) 1.52-1.53 (d, 3H), 1.68-1.78 (m, 1H), 1.82-1.91 (q, 1H), 1.95-2.05 (m, 1H), 2.16-2.37 (m, 3H), 2.38-2.50 (m, 2H), 2.44 (s, 3H), 2.81-2.87 (t, 1H), 2.83 (s, 3H), 2.90-2.99 (m, 2H), 3.11-3.18 (dt, 1H), 3.48-3.60 (m, 3H), 3.66-3.69 (d, 1H), 3.89-3.96 (m, 1H), 4.15-4.19 (dd, 1H), 4.33-4.36 (dd, 1H), 5.40-5.45 (q, 1H), 6.26 (s, 2H), 6.76-6.81 (dt, 1H), 6.85-6.88 (dd, 1H), 7.27-7.31 (dd, 1H), 7.70 (s, 2H), 7.88 (s, 1H).

(M+H)$^+$ Calcd for C$_{31}$H$_{35}$F$_7$N$_4$O 629, found 629.
XRD pattern of Example 1 is disclosed in FIG. 4.
DSC thermogram of Example 1 is disclosed in FIG. 5.

EXAMPLE 1a

Preparation of Amorphous Orvepitant Maleate

Orvepitant Hydrochloride (1.00 G) Was Suspended In Ethyl Acetate (20 Ml) And Water (10 ml) and 25% w/w ammonia (10 ml) were added. The aqueous layer was separated and the organic layer was washed with 10% w/w sodium chloride solution (2×10 ml). The organic solution was separated, evaporated to dryness and isopropanol (20 ml) was added. The solution was evaporated to dryness. The material was diluted with isopropanol (6 ml) and a solution of maleic acid (0.174 g) in isopropanol (2.0 ml) was added. Iso-octane (a total of 8 ml) was added and the solution was stirred overnight. The solution was evaporated to an oil. Tert-butyl methyl ether (10 ml) was added and the solution was evaporated to dryness. Repeat the addition of tert-butyl methyl ether and evaporation a total of 4 times. On final evaporation, a foam forms that solidifies to give the title compound.

NMR (CD$_3$OD) δ (ppm) 1.51-1.53 (d, 3H), 1.68-1.77 (m, 1H), 1.80-1.89 (q, 1H), 1.93-2.02 (m, 1H), 2.14-2.37 (m, 3H), 2.38-2.50 (m, 2H), 2.44 (s, 3H), 2.77-2.83 (t, 1H), 2.83 (s, 3H), 2.90-2.96 (m, 2H), 3.09-3.15 (dt, 1H), 3.45-3.59 (m, 3H), 3.63-3.66 (d, 1H), 3.87-3.94 (m, 1H), 4.14-4.18 (dd, 1H), 4.32-4.36 (dd, 1H), 5.40-5.45 (q, 1H), 6.26 (s, 2H), 6.76-6.81 (dt, 1H), 6.85-6.89 (dd, 1H), 7.27-7.31 (dd, 1H), 7.69 (s, 2H), 7.88 (s, 1H).

EXAMPLE 1b

Preparation of Orvepitant Maleate A

Method A

A stirred slurry of orvepitant hydrochloride (6.65 g) in ethyl acetate (93 ml) was treated with water (47 ml) and 880 aqueous ammonia solution (47 ml). After stirring at room temperature for 10 mins the organic phase was separated and washed with water (3×47 ml). The organic phase was evaporated to a white foam (6.323 g). The foam was dissolved in THF (74 ml) and the clear colourless solution was treated with maleic acid (1.161 g). The solution was heated at reflux for 1 h and then the solution was divided into two equal portions. To one of the portions more maleic acid (290 mg) was added and the mixture was heated at reflux. After 0.75 h iso-octane (37 ml) was added and the mixture allowed to cool to room temperature giving a slightly hazy solution.

A small sample of orvepitant maleate amorphous Example 1a was heated on a microscope slide on a hot plate giving a brown melt. This was allowed to cool and appeared to crystallise. This solid was scraped off the slide.

The solid from the microscope slide was used as seed for the above hazy solution, which quickly crystallised giving a thick slurry. The slurry was stirred over night and was then heated to about 70° C. After 1 h the slurry was allowed to cool to room temperature and then after a further 2 h the product was collected, washed with 1:1 THF/iso-octane (3×5 ml), briefly pulled dry and then dried in vacuo at room temperature to obtain a solid orvepitant maleate A (3.782 g).

NMR (CDCl$_3$) δ (ppm) 1.42-1.44 (d, 3H), 1.60-1.70 (m, 1H), 1.84-1.93 (q, 1H), 1.93-2.01 (m, 1H), 2.12-2.15 (d, 1H), 2.21-2.25 (d, 1H), 2.30-2.40 (m, 1H), 2.41 (s, 3H), 2.42-2.51 (m, 3H), 2.73 (s, 3H), 2.72-2.77 (m, 1H), 2.94-3.00 (t, 1H), 3.26-3.32 (t, 1H), 3.36-3.50 (m, 3H), 3.58-3.60 (d, 1H), 4.03-

4.10 (m, 1H), 4.19-4.23 (dd, 1H), 4.31-4.34 (dd, 1H), 5.49-5.54 (q, 1H), 6.29 (s, 2H), 6.80-6.86 (m, 2H), 7.15-7.19 (dd, 1H), 7.55 (s, 2H), 7.78 (s, 1H).

Method B

{(1R)-1-[3,5-bis(trifluoromethyl)phenyl]ethyl}methylamine-(2R)-2-hydroxybutanedioic acid (90 kg) was added to ethyl acetate (270 litres) and 15% w/w sodium carbonate solution (310 kg) and was stirred until all solids had dissolved. The organic phase was separated and was washed with water (270 litres). Fresh ethyl acetate (336 litres) was added and the solution was distilled to ca270 litres under reduced pressure. More ethyl acetate (336 litres) was added and the solution was distilled to ca270 litres under reduced pressure.

The solution was diluted with ethyl acetate (180 litres). The reactor was purged with carbon dioxide and a continuous steady stream of carbon dioxide was maintained. Triethylamine (29.8 kg) was added over ca30 minutes and was rinsed in with ethyl acetate (15 litres). The reaction mixture was stirred for ca30 minutes. Chlorotrimethylsilane (36.2 kg) was added over ca30 minutes with cooling to keep the temperature at ca20° C. and was rinsed in with ethyl acetate (15 litres). The reaction mixture was stirred for ca30 minutes. Pyridine (35.2 kg) was added and was rinsed in with ethyl acetate (30 litres). Thionyl chloride (39.1 kg) was added and then a rinse of ethyl acetate (30 litres). The reaction mixture was stirred at ca20° C. for ca16 hours under a carbon dioxide atmosphere.

28% w/w Racemic malic acid solution (302 kg) was added and the mixture was stirred for ca15 minutes. The organic phase was separated, diluted with ethyl acetate (90 litres) and was washed with water (2×135 litres) and 20% w/w dibasic potassium phosphate solution (316 kg). The solution was distilled under reduced pressure to a total volume of ca150 litres. Ethyl acetate (300 litres) was added and the solution was re-distilled to ca150 litres to give a solution of {(1R)-1-[3,5-bis(trifluoromethyl)phenyl]ethyl}methylcarbamic chloride.

Ethyl acetate (240 litres) was cooled to α-10° C. and (2R)-2-(4-fluoro-2-methylphenyl)-4-piperidinone-(2S)-hydroxy(phenyl)ethanoic acid (60 kg) was charged. The slurry was warmed to ca0° C. and 15% w/w sodium carbonate solution (275 kg) was added, The mixture was stirred until all solids dissolved.

The organic phase was separated and was washed with 20% w/w sodium chloride solution (274 kg). Fresh ethyl acetate (240 litres) was added and the solution of (2R)-2-(4-fluoro-2-methylphenyl)-4-piperidinone was distilled under reduced pressure to a volume of ca180 litres.

The solution of {(1R)-1-[3,5-bis(trifluoromethyl)phenyl]ethyl}methylcarbamic chloride was charged to the solution of (2R)-2-(4-fluoro-2-methylphenyl)-4-piperidinone followed by an ethyl acetate (60 litre) rinse. Triethylamine (43 kg) was added followed by ethyl acetate (12 litres) and the mixture was boiled at reflux for a total of ca23 hours. The slurry was cooled to ca20° C. and N-acetylpiperazine (12 kg) and ethyl acetate (12 litres) were added. The reaction mixture was stirred for ca30 minutes and was then charged with 28% w/w racemic malic acid solution (202 kg). The organic phase was separated and was washed with 20% w/w sodium chloride solution (274 litres). Ethyl acetate (240 litres) was added and the solution of (2R)—N-{(1R)-1-[3,5-bis(trifluoromethyl)phenyl]ethyl}-2-(4-fluoro-2-methylphenyl)-N-methyl-4-oxo-1-piperidinecarboxamide was distilled under reduced pressure distillation to a total volume of ca180 litres.

(8aS)-hexahydropyrrolo[1,2-a]pyrazin-6(2H)-one-(2S)-(acetyloxy)(phenyl)ethanoic acid (75 kg) was added to acetonitrile (570 litres) and triethylamine (22.7 kg) was added. An acetonitrile (15 litre) rinse was added and the slurry was stirred at ca20° C. for ca30 min. Sodium triacetoxyborohydride (45 kg) was added and the reaction was cooled to ca20° C. Formic acid (24.2 kg) was added to the mixture over ca2 hours, maintaining the temperature below 15° C. An acetonitrile (15 litre) rinse was added and the reaction was warmed to ca20° C. The solution of (2R)—N-{(1R)-1-[3,5-bis(trifluoromethyl)phenyl]ethyl}-2-(4-fluoro-2-methylphenyl)-N-methyl-4-oxo-1-piperidinecarboxamide in ethyl acetate was added to the reaction mixture and was rinsed in with acetonitrile (60 litre). The reaction was stirred for ca32 hours at ca20° C.

The slurry was distilled to ca300 litres under reduced pressure. The mixture was diluted with ethyl acetate (600 litres) and was washed with 13% w/w ammonia solution (228 kg and 221 kg), and then 10% w/w sodium chloride solution (256 kg).

The organic solution was distilled to ca300 litres under reduced pressure. The solution was diluted with IPA (480 litres) and was distilled under reduced pressure to ca300 litres. Further IPA (480 litres) was added and the solution was again distilled to ca300 litres. The solution was diluted with IPA (80 litres).

A solution of maleic acid (16.4 kg) in IPA (150 litres) was added and rinsed in with more IPA (6 litres). The mixture was then seeded with orvepitant maleate Form 2 (60 g), and the mixture was aged for ca2.5 hours. Iso-octane (510 litres) was added over ca50 minutes and the mixture further aged for ca1 hour. The slurry was cooled to ca5 to 10° C. and was further aged for ca90 minutes. The solid formed was filtered and washed with a 1:1 mixture of IPA/iso-octane (2×180 litres). The resulting solid was dried at 50° C. under reduced pressure to give 87.0 kg of a 63.8:36.6 mixture of (2R,4S)—N-{(1R)-1-[3,5-bis(trifluoromethyl)phenyl]ethyl}-2-(4-fluoro-2-methylphenyl)-N-methyl-4-[(8aS)-6-oxohexahydropyrrolo[1,2-a]pyrazin-2(1H)-yl]-1-piperidinecarboxamide maleate and (2R,4R)—N-{(1R)-1-[3,5-bis(trifluoromethyl)phenyl]ethyl}-2-(4-fluoro-2-methylphenyl)-N-methyl-4-[(8aS)-6-oxohexahydropyrrolo[1,2-a]pyrazin-2(1H)-yl]-1-piperidinecarboxamide maleate. 1.00 kg of this solid was slurried in MIBK (8 L) and stirred at 20-25° C. for 23 hours and 30 min. The slurry was then filtered under vacuum. The filtrate was concentrated under vacuum (35 mbar, maintaining temperature<45° C.) to a volume of ca. 2.0 litres. 2-Methyl tetrahydrofuran (9 L) was then added, maintaining the temperature at 45±5° C. throughout addition. The solution was heated to 65 to 70° C. to ensure complete dissolution and then cooled to 40 to 45° C. prior to seeding with orvepitant maleate A (0.635 g). The slurry was cooled to 20 to 25° C. over ca. 2 h and was then stirred at this temp for ca. 15.5 h. The product was collected by vacuum filtration, the filter cake was washed with 2Me-THF/MIBK (6:1, 2×1.27 L), and was then dried under vacuum at ca. 50° C. to give 500 g of orvepitant maleate A Onset melt 112° C. by DSC.

NMR (CD$_3$OD) δ (ppm) 1.51-1.53 (d, 3H), 1.68-1.78 (m, 1H), 1.79-1.88 (q, 1H), 1.92-2.02 (m, 1H), 2.14-2.37 (m, 3H), 2.40-2.50 (m, 2H), 2.44 (s, 3H), 2.76-2.84 (t, 1H), 2.83 (s, 3H), 2.88-2.96 (m, 2H), 3.08-3.15 (dt, 1H), 3.43-3.59 (m, 3H), 3.62-3.65 (d, 1H), 3.86-3.93 (m, 1H), 4.14-4.18 (dd, 1H), 4.32-4.36 (dd, 1H), 5.40-5.45 (q, 1H), 6.26 (s, 2H), 6.76-6.81 (dt, 1H), 6.85-6.88 (dd, 1H), 7.27-7.30 (dd, 1H), 7.69 (s, 2H), 7.88 (s, 1H).

Orvepitant maleate A is an intermediate grade crystallisation product. It is a variable mixture of orvepitant maleate Form 2 and orvepitant maleate solvated forms.

EXAMPLE 2

Preparation of the Form 1 of Orvepitant Maleate

A mixture of {(1R)-1-[3,5-bis(trifluoromethyl)phenyl]ethyl}methylamine-(2R)-2-hydroxybutanedioic acid (67.5 g) in ethyl acetate (200 ml) was treated with a solution of sodium carbonate (26 g) in water (200 ml). The mixture was stirred until all the solids had dissolved. The organic layer was separated and was washed with water (200 ml). The organic phase was diluted with more ethyl acetate (250 ml) and was then concentrated to 250 ml in vacuo. The organic phase was then diluted with more ethyl acetate (250 ml) and then was re-concentrated to 250 ml in vacuo.

The solution was transferred to a flask, washing in with ethyl acetate (2×5 ml) and then the flask was flushed with a stream of carbon dioxide. The flask was then charged with triethylamine (30.5 ml) over 6 min. After 36 min trimethylsilyl chloride (32 ml) was added over 29 min. After a further 50 min pyridine (27 ml) was added over 1 min. After a further 8 min thionyl chloride (18 ml) was added over 4 min. The mixture was stirred overnight at ambient temperature under a carbon dioxide atmosphere. The reaction mixture was treated with a solution of malic acid (28 g) in water (100 ml) over 10 min with ice bath cooling. After stirring for 15 min the aqueous phase was separated. The organic phase was washed with water (100 ml) and then a solution of sodium carbonate (19.5 g) in water (150 ml). The organic phase was diluted with more ethyl acetate (150 ml) and concentrated to 125 ml in vacuo. More ethyl acetate (150 ml) was added and then the solution was re-concentrated to 125 ml (Solution A).

(2R)-2-(4-fluoro-2-methylphenyl)-4-piperidinone-(2S)-hydroxy(phenyl)ethanoic acid (50 g) was added to a stirred mixture of ethyl acetate (200 ml), water (200 ml) and sodium carbonate (26 g). When clear solutions had formed the organic phase was separated and was washed with a solution of sodium chloride (40 g) in water (200 ml). The organic phase was diluted with more ethyl acetate (200 ml) and concentrated to 125 ml in vacuo. (Solution B).

Solution B was treated with triethylamine (49 ml) and then Solution A was added washing in with ethyl acetate (2×2 ml). The mixture was heated to ca 76° C. After ca 18 hours the mixture was treated with N-acetyl piperazine (10 g) washing in with ethyl acetate (2×2 ml). After stirring for 20 min a solution of malic acid (42 g) in water (150 ml) was added. After stirring for 5 min the organic phase was separated and was washed with a solution of sodium chloride (40 g) in water (200 ml). The organic phase was diluted with acetonitrile (200 ml) and was concentrated to 125 ml in vacuo. More acetonitrile (200 ml) was added and the solution was concentrated to 150 ml in vacuo. (Solution C).

Sodium triacetoxyborohydride (18.75 g) was added to a stirred slurry of (8aS)-hexahydropyrrolo[1,2-a]pyrazin-6(2H)-one-(2S)-(acetyloxy)(phenyl)ethanoic acid (31.25 g) in acetonitrile (250 ml) and triethylamine (13 ml) under nitrogen. The mixture was cooled to less than 10° C. and was treated with formic acid (8.25 ml) at less than 15° C. A portion of Solution C (62 g) was added over 10 min and the mixture allowed to warm to ambient temperature. After ca 24 h the reaction mixture was concentrated to ca 150 ml in vacuo. Ethyl acetate (225 ml) was added and the solution was washed with 13% w/v aqueous ammonia solution (2×100 ml) and 10% w/v aqueous sodium chloride solution (100 ml). The organic phase was concentrated to ca 125 ml in vacuo and was diluted with iso-propanol (200 ml). The mixture was concentrated to ca 120 ml in vacuo. More iso-propanol (200 ml) was added and the concentration was repeated. The concentrate was diluted with iso-propanol to give a total volume of 125 ml (Solution D).

A portion of Solution D (25 ml) was charged to a flask and diluted with IPA (10.3 ml). The solution was treated over 5 min with a solution of maleic acid (1.237 g) in IPA (9.1 ml), washing in with IPA (1.2 ml). The solution was warmed to ca 60° C. and treated with iso-octane (41.3 ml). The mixture was cooled to ca 49° C. and seeded with orvepitant maleate, Form 1 (10 mg prepared according Example 5) The mixture was cooled to ca 35° C. and stirred overnight. The slurry was cooled to ca 7° C. After a further 2.5 hours the product was collected by vacuum filtration. The bed was washed with 1:1 IPA/iso-octane (2×10 ml), briefly pulled dry and then the solid was dried in vacuo at ca 50° C. to afford Form 1 orvepitant maleate. Yield: 2.886 g. mp 183-185° C. (determined using an Electrothermal IA9000 series melting point apparatus. Values were uncorrected).

NMR (CD$_3$OD) δ (ppm) 1.51-1.53 (d, 3H), 1.67-1.77 (m, 1H), 1.78-1.87 (q, 1H), 1.91-2.01 (m, 1H), 2.13-2.22 (m, 2H), 2.25-2.34 (m, 1H) 2.36-2.50 (m, 2H), 2.44 (s, 3H), 2.74-2.80 (t, 1H), 2.83 (s, 3H), 2.86-2.96 (m, 2H), 3.06-3.13 (dt, 1H), 3.41-3.59 (m, 3H), 3.61-3.64 (d, 1H), 3.84-3.91 (m, 1H), 4.13-4.18 (dd, 1H), 4.32-4.36 (dd, 1H), 5.40-5.45 (q, 1H), 6.26 (s, 2H), 6.76-6.81 (dt, 1H), 6.86-6.89 (dd, 1H), 7.27-7.30 (dd, 1H), 7.70 (s, 2H), 7.88 (s, 1H).

EXAMPLE 3

Preparation of Form 1 of Orvepitant Maleate

A slurry of orvepitant maleate A Example 1b method A (500 mg) in iso-octane (10 ml) was stirred and heated at 98-99° C. (reflux) overnight. The slurry was allowed to cool to ambient temperature. The product was collected by vacuum filtration, washed with iso-octane, briefly deliquored and then dried in vacuo at ca 50° C. to afford Form 1 orvepitant maleate. Yield: 365 mg.

Onset melt combined with degradation=181° C. by DSC

NMR (CD$_3$OD) δ (ppm) 1.51-1.53 (d, 3H), 1.67-1.77 (m, 1H), 1.78-1.87 (q, 1H), 1.91-2.01 (m, 1H), 2.13-2.22 (m, 2H), 2.25-2.34 (m, 1H) 2.36-2.50 (m, 2H), 2.44 (s, 3H), 2.74-2.80 (t, 1H), 2.83 (s, 3H), 2.86-2.96 (m, 2H), 3.06-3.13 (dt, 1H), 3.41-3.59 (m, 3H), 3.61-3.64 (d, 1H), 3.84-3.91 (m, 1H), 4.13-4.18 (dd, 1H), 4.32-4.36 (dd, 1H), 5.40-5.45 (q, 1H), 6.26 (s, 2H), 6.76-6.81 (dt, 1H), 6.86-6.89 (dd, 1H), 7.27-7.30 (dd, 1H), 7.70 (s, 2H), 7.88 (s, 1H).

EXAMPLE 4

Preparation of the Form 1 of Orvepitant Maleate

Example 1 (1.00 kg) was dissolved in methyl iso-butyl ketone (MIBK) (9.0 l) and warmed to 50-55° C. The solution was filtered into a clean warm vessel washing through with MIBK (1.0 l). The solution was reheated to 70-75° C. and iso-octane (5 l) was added over 40 minutes. The solution was cooled to 55-57° C. and orvepitant maleate (Form 1 seed, 10 g) was added. After stirring for 1.5 hours the slurry was cooled to 23-27° C. and more iso-octane (5.0 l) was added. The slurry was stirred at 23-27° C. for 16 hours and the product isolated by filtration, washed twice with a mixture of iso-octane (1 l) and MIBK (1 l). The solid was dried at 50° C. in a vacuum oven to give orvepitant maleate, Form 1 (908 g, 90.8% th). Onset melt combined with degradation.=186° C. by DSC.

NMR (CD$_3$OD) δ (ppm) 1.52 (d, 3H), 1.69-1.76 (m, 1H), 1.84 (q, 1H), 1.93-2.01 (m, 1H), 2.13-2.18 (m, 1H), 2.19-2.24 (m, 1H), 2.27-2.33 (m, 1H), 2.37-2.49 (m, 2H), 2.44 (s, 3H), 2.77 (t, 1H), 2.83 (s, 3H), 2.87-2.97 (m, 2H), 3.11 (dt, 1H), 3.41-3.48 (m, 1H), 3.50 (d, 1H), 3.56 (dt, 1H), 3.62 (d, 1H), 3.86-3.92 (m, 1H), 4.15 (dd, 1H), 4.34 (dd, 1H), 5.42 (q, 1H), 6.26 (s, 2H), 6.78 (dt, 1H), 6.87 (dd, 1H), 7.28 (dd, 1H), 7.69 (s, 2H), 7.87 (s, 1H).

HRMS calcd for C$_{31}$H$_{35}$F$_7$N$_4$O$_2$ 629.2721 found 629.2770.

Anal. Calcd for C$_{31}$H$_{35}$F$_7$N$_4$O$_2$.C$_4$H$_4$O$_4$: C, 56.5; H, 7.5; F, 5.3; N, 17.9. Found: C, 56.5; H, 7.4; F, 5.1; N, 18.0.

EXAMPLE 5

Preparation of the Form 1 of Orvepitant Maleate

IPA solution (total of 70 ml) containing (2R,4S)—N-{(1R)-1-[3,5-bis(trifluoromethyl)phenyl]ethyl}-2-(4-fluoro-2-methylphenyl)-N-methyl-4-[(8aS)-6-oxohexahydropyrrolo[1,2-a]pyrazin-2(1H)-yl]-1-piperidinecarboxamide (10.01 g) and (2R,4 R)—N-{(1R)-1-[3,5-bis(trifluoromethyl)phenyl]ethyl}-2-(4-fluoro-2-methylphenyl)-N-methyl-4-[(8aS)-6-oxohexahydropyrrolo[1,2-a]pyrazin-2(1H)-yl]-1-piperidinecarboxamide (4.27 g) was diluted with IPA (23.8 ml). Maleic acid (2.85 g) in IPA (21 ml) was added, was washed in with IPA (2.8 ml) and was seeded with orvepitant maleate A (10 mg). The slurry was stirred for 1 hour. Isooctane (95 ml) was added dropwise over 15 minutes and the slurry was stirred for a further 1 hour. The mixture was cooled to 7-10° C. and was filtered, washed with a 1:1 mixture of IPA and isooctane and was dried in vacuo at about 50° C. Yield 10.88 g. 2.0 g of this was dissolved in IPA (20 ml), was heated to give a clear colourless solution, allowed to cool to about 50° C., seeded (10 mg of example 3 Form 1) and was then allowed to cool. This gave a very thick unstirrable slurry which was reheated to give a solution. Isooctane (20 ml) was added at 60° C., cooled to about 50° C. and was reseeded (10 mg example 3 Form 1). The hazy solution was stirred overnight at about 50° C. and was allowed to cool to about 20° C. After 5 hours, the solid was collected by vacuum filtration, was washed with a mixture of 1:1 of IPA and iso-octane (2×2 ml, 2×1 ml) and was dried in vacuum at 50° C. Yield 1.546 g.

Onset melt combined with degradation=183° C. by DSC.

NMR (CD$_3$OD) δ (ppm) 1.51-1.53 (d, 3H), 1.67-1.77 (m, 1H), 1.79-1.87 (q, 1H), 1.91-2.01 (m, 1H), 2.14-2.37 (m, 3H), 2.39-2.50 (m, 2H), 2.44 (s, 3H), 2.73-2.79 (t, 1H), 2.83 (s, 3H), 2.86-2.96 (m, 2H), 3.06-3.13 (dt, 1H), 3.40-3.58 (m, 3H), 3.60-3.63 (d, 1H), 3.84-3.91 (m, 1H), 4.13-4.17 (dd, 1H), 4.32-4.36 (dd, 1H), 5.40-5.45 (q, 1H), 6.26 (s, 2H), 6.76-6.81 (dt, 1H), 6.86-6.89 (dd, 1H), 7.27-7.30 (dd, 1H), 7.70 (s, 2H), 7.88 (s, 1H).

EXAMPLE 6

Preparation of the Form 1 of Orvepitant Maleate

Orvepitant maleate A (25 Kg) was dissolved in methyl iso-butyl ketone (MIBK) (100 Kg) with warming to ca. 70° C. The solution was passed through a filter into a clean, warm vessel and the process lines were washed through with warm MIBK (20 Kg). The resultant MIBK solution was reheated to ca. 70° C. Filtered iso-octane (10.4 Kg) was added at ca. 70° C. over 17 min. The solution was cooled to ca 60° C., seeded using a pre-prepared slurry of orvepitant maleate Form 1 (0.158 Kg prepared according to Example 4) in iso-octane (0.7 Kg), followed by an iso-octane wash (1.4 Kg) of the seeding container, and stirred at ca 60° C. for ca. 1 hour. More filtered iso-octane (17.2 Kg) was added over ca. 80 min, and then stirred for ca. 30 min. More filtered iso-octane (17.3 Kg) was added over ca. 1.5 hours and the resultant slurry stirred for ca. 0.5 hours. More filtered iso-octane (6.9 Kg) was added over 0.5 hours. After stirring for a further ca. 15 hours more iso-octane (103.5 Kg) was added over ca. 2 hours and the slurry stirred for ca. 1 hour at ca. 60° C. The slurry was cooled to ca. 26° C. over 2 hours. After stirring for ca. 11.5 hours at ca. 26° C. the product was collected by vacuum filtration. The filter cake was washed twice with filtered MIBK-iso-octane (each wash prepared from MIBK 20 Kg iso-octane 25.9 Kg), deliquored and then dried in a vacuum oven at ca 50° C. to give the title compound (21.5 Kg, 86%).

Onset melt combined with degradation=185° C. by DSC

NMR (CD$_3$OD) δ (ppm) 1.51-1.53 (d, 3H), 1.68-1.78 (m, 1H), 1.85-1.93 (q, 1H), 1.97-2.07 (m, 1H), 2.18-2.37 (m, 3H), 2.40-2.48 (m, 2H), 2.46 (s, 3H), 2.83-2.88 (t, 1H), 2.83 (s, 3H), 2.91-3.01 (m, 2H), 3.13-3.21 (dt, 1H), 3.51-3.59 (m, 3H), 3.68-3.71 (d, 1H), 3.92-3.99 (m, 1H), 4.15-4.19 (dd, 1H), 4.34-4.37 (dd, 1H), 5.40-5.46 (q, 1H), 6.25 (s, 2H), 6.76-6.81 (dt, 1H), 6.85-6.88 (dd, 1H), 7.27-7.31 (dd, 1H), 7.69 (s, 2H), 7.87 (s, 1H).

EXAMPLE 7

Preparation of the Form 1 of Orvepitant Maleate

Example 1b Method B (12 kg) was dissolved in methyl iso-butyl ketone (MIBK) (ca. 60.4 L) by warming to 70-75° C. The solution was filtered into a clean, warm vessel washing through with warm MIBK (ca. 12 L). The solution was reheated to 70-75° C. in order to redissolve any crystalline material. Iso-octane (ca. 10 kg) was added over ca. 10 min maintaining 70-75° C. The solution was cooled to ca. 60° C., seeded (ca. 24 g of Form 1 seed slurried in 0.24 L filtered iso-octane) and held at ca 60° C. for ca. 0.5 hours. Iso-octane (64.8 kg) was added over ca. 3 hours maintaining the temperature at ca. 60° C. After ca. 63 min age at ca. 60° C. the slurry was cooled to ca. 25° C. over ca. 2 h. After a further ca. 1 h age, the product was collected by filtration. The bed was first washed with filtered 2:3 MIBK/iso-octane (1×57 L), and a second time with neat iso-octane (1×57 L), pulled dry and then dried at 45-55° C. Yield 93.8% th.

Onset melt combined with degradation=185° C. by DSC.

NMR (CD$_3$OD) δ (ppm) 1.52-1.54 (d, 3H), 1.72-1.78 (m, 1H), 1.83-1.90 (q, 1H), 1.96-2.03 (m, 1H), 2.17-2.19 (dd, 1H), 2.22-2.25 (d, 1H), 2.28-2.36 (m, 1H), 2.39-2.51 (m, 2H), 2.46 (s, 3H), 2.77-2.81 (t, 1H), 2.85 (s, 3H), 2.90-2.98 (m, 2H), 3.10-3.16 (dt, 1H), 3.44-3.48 (m, 1H), 3.52-3.55 (m, 1H), 3.57-3.61 (m, 1H), 3.64-3.66 (d, 1H), 3.89-3.94 (m, 1H), 4.16-4.19 (dd, 1H), 4.35-4.38 (dd, 1H), 5.43-5.46 (q, 1H), 6.28 (s, 2H), 6.79-6.82 (dt, 1H), 6.87-6.90 (dd, 1H), 7.29-7.32 (dd, 1H), 7.71 (s, 2H), 7.89 (s, 1H).

EXAMPLE 8

Preparation of the Form 1 of Orvepitant Maleate

Orvepitant maleate A (550 g) was dissolved in methyl iso-butyl ketone (MIBK) (2.76 l) and warmed to 70-75° C. The solution was filtered into a clean warm vessel washing through with MIBK (0.55 l). The solution was reheated to 70-75° C. and isooctane (0.33 l) was added over 9 minutes. The contents were held at 70-75° C. to ensure complete solution. The solution was cooled to 60-65° C., orvepitant maleate (Form 1 seed, 3.47 g prepared according to Example 4) was added and the contents were stirred for 1 hour at 57 to 63° C. More isooctane (1.32 l) was added over 3 hours 45 min maintaining the temperature at 57 to 63° C. The slurry was stirred at 57 to 63° C. for 17.5 hours. More isooctane (3.31 l) was added to the slurry over 2 hours maintaining the temperature at 57 to 63° C. and the mixture was stirred for 1 hour. The slurry was cooled to 22 to 28° C. over 2 hours and was stirred for 1 hour. The product was isolated by filtration, washed twice with a mixture of isooctane (0.83 l) and MIBK (0.55 l). The solid was dried at 50° C. in a vacuum oven to give orvepitant maleate, Form 1 (519 g, 94.3% th).

Onset melt combined with degradation=185° C. by DSC.

NMR (CD$_3$OD) δ (ppm) 1.51-1.53 (d, 3H), 1.68-1.77 (m, 1H), 1.80-1.89 (q, 1H), 1.94-2.03 (m, 1H), 2.15-2.37 (m, 3H), 2.38-2.51 (m, 2H), 2.44 (s, 3H), 2.78-2.84 (t, 1H), 2.83 (s, 3H), 2.90-2.96 (m, 2H), 3.09-3.16 (dt, 1H), 3.46-3.59 (m, 3H), 3.64-3.67 (d, 1H), 3.87-3.95 (m, 1H), 4.14-4.18 (dd, 1H), 4.32-4.36 (dd, 1H), 5.40-5.45 (q, 1H), 6.26 (s, 2H), 6.76-6.81 (dt, 1H), 6.85-6.88 (dd, 1H), 7.27-7.31 (dd, 1H), 7.70 (s, 2H), 7.88 (s, 1H).

X-Ray Powder Diffraction. (XRD)

The XRD pattern was determined on a PANalytical X'-Pert Pro powder diffractometer model PW3040/60 using an X'Celerator detector equipped with a monochromator using copper Kα X-radiation. The acquisition conditions were: generator tension: 40 kV, generator current: 45 mA, start angle: 2.0° 2 Theta, end angle: 40.0° 2 Theta, step size: 0.0167° 2θ, time per step: 31.75 seconds.

The sample was prepared by mounting a few milligrams of Example 5 on a silicon wafer (zero background) plates, resulting in a thin layer of powder.

The Pattern is provided in FIG. 1.

Form 1 orvepitant maleate can be identified by certain characteristic 2 theta angle peak at 7.3±0.1, 7.5±0.1, 10.9±0.1, 12.7±0.1, 16.5±0.1 degrees, which correspond respectively to d-spacings at 12.2, 11.8, 8.1, 7.0 and 5.4 Angstroms (Å)

Form 1 orvepitant maleate typically exhibits 2 theta angle peaks at essentially the following positions 7.3±0.1, 7.5±0.1, 10.7±0.1, 10.9±0.1, 12.7±0.1, 15.0±0.1, 15.3±0.1, 16.5±0.1, 17.0±0.1, 17.5±0.1, 19.3±0.1, 19.6±0.1, 20.1±0.1, 20.3±0.1, 20.9±0.1, 21.1±0.1, 21.8±0.1, 22.6±0.1 degrees, which correspond respectively to d-spacings 12.2, 11.8, 8.3, 8.1, 7.0, 5.9, 5.8, 5.4, 5.2, 5.1, 4.6, 4.5, 4.4, 4.4, 4.3, 4.2, 4.1, 3.9 Angstroms (Å).

Thermal Analysis.

Differential scanning calorimetry (DSC) was carried out on a TA Q1000 calorimeter. The sample of Example 6 was weighed into an aluminium pan, a pan lid placed on top and light crimped without sealing the pan. Scan rate of 10° C. per minute. Sample size of between 1 and 2 mg. The thermogram of orvepitant maleate Form 1 is provided at FIG. 2.

When reporting DSC data, the onset or peak temperature of an event can be reported. In the current filling, onset temperatures are only reported. The onset temperature is the intersection of the leading event tangent with the baseline.

Moderately sharp asymmetric melting endotherm with onset temperature of 185° C. combined with the decomposition.

When the melt is combined with the degradation, the person skill in the art will appreciate that small variation in the onset melt temperature may be observed with different batches of the same material.

Solid State Nuclear Magnetic Resonance.

$^{13}$C solid-state NMR data of FIG. 3 was acquired using a Bruker spectrometer operating at a frequency of 90.55 MHz for $^{13}$C observation. A 4-mm Bruker HFX MAS (magic-angle spinning) probe was used. The Example 4 was gently packed into a zirconia rotor and spun at 10 kHz, at a temperature of 296K. Data was obtained using ramped cross-polarization and a TOSS (total sideband suppression) pulse sequence. Proton decoupling was performed at an RF power of 100 kHz using the SPINAL64 decoupling sequence. Characteristic $^{13}$C NMR peak positions are reported in parts per million (ppm) frequency relative to tetramethylsilane at 0 ppm, and have a precision of +/−0.3 ppm caused by instrumental variability and calibration.

Pharmaceutical Compositions

Orvepitant maleate Form 1 will normally, but not necessarily, be formulated into pharmaceutical compositions prior to administration to a patient. In one aspect, the invention is directed to pharmaceutical compositions comprising Orvepitant maleate Form 1.

Tablets of orvepitant maleate Form 1 have been formulated as white to off-white, film-coated round tablets containing 10 mg, 30 mg, 50 mg and 60 mg of orvepitant which provide an immediate release of the active ingredient for oral administration.

The list of excipients and quantitative composition of tablets are reported in Table 1 below.

TABLE 1

Composition of Tablets Orvepitant Maleate

| Component | Quantity (mg/tablet) | | | | Function |
| --- | --- | --- | --- | --- | --- |
| | 10 mg | 30 mg | 50 mg | 60 mg | |
| Tablet core | | | | | |
| Orvepitant maleate Form1 | 11.85[1] | 35.54[2] | 59.23[3] | 71.09[4] | Active |
| Microcrystalline cellulose | 60.00 | 149.22 | 60.00 | 79.39 | Filler |
| Lactose monohydrate | 201.90 | 95.54 | 154.52 | 122.12 | Filler |
| Croscarmellose sodium | 9.00 | 5.92 | 9.00 | 11.85 | Disintegrant |
| Hypromellose | 15.00 | 10.78 | 15.00 | 12.55 | Binder |
| Magnesium stearate | 2.25 | 3.00 | 2.25 | 3.00 | Lubricant |
| Purified water[5] | qs | qs | qs | qs | Granulating fluid |
| Total unit dose | 300.00 | 300.0 | 300.00 | 300.0 | — |
| Coat | | | | | |
| Opadry ® White OY-S-28876 | 9.00 | 9.00 | 9.00 | 9.0 | Coating agent |

TABLE 1-continued

Composition of Tablets Orvepitant Maleate

| Component | Quantity (mg/tablet) | | | | Function |
|---|---|---|---|---|---|
| | 10 mg | 30 mg | 50 mg | 60 mg | |
| Purified water[5] | qs | qs | qs | qs | Suspending agent |

Note:
[1]Corresponding to 10.0 mg as orvepitant
[2]Corresponding to 30.0 mg as orvepitant
[3]Corresponding to 50.0 mg as orvepitant
[4]Corresponding to 60.0 mg as orevepitant
[5]Removed during processing. Does not appear in the final product.

Orvepitant maleate tablets, 10 mg, 30 mg, 50 mg and 60 mg were manufactured using wet granulation, dry blending, tablet compression and film coating processes. Drug substance, lactose monohydrate, microcrystalline cellulose and croscarmellose sodium were sieved and dry mixed into the high shear mixer granulator for approximately 5 minutes. The granulation water was sprayed onto the drug substance, lactose monohydrate, microcrystalline cellulose and croscarmellose sodium dry blend. The wet granule was dried approximately at 65° C. into a fluid bed dryer for approximately 45 minutes (<2% LOD), milled using a conical mill (screen size 813 μm) and blended into a bin blender with lactose monohydrate, microcrystalline cellulose and croscarmellose sodium for approximately 20 minutes. Magnesium stearate was added for lubrication into the bin blender and the mixture was blended for approximately 3 minutes.

The blend was compressed using a suitable rotary tablet compression machine to obtain uncoated tablets. Opadry® White OY-S-28876 was charged into a mixing vessel with purified water and the film coating suspension prepared with stirring. The tablets were film coated into a suitable pan coater (approximately 3% weight gain).

What is claimed is:

1. Anhydrous crystalline orvepitant maleate, comprising X-ray powder diffraction pattern peaks at 7.3±0.1, 7.5±0.1, 10.9±0.1, 12.7±0.1, and 16.5±0.1 degrees 2 theta.

2. Anhydrous crystalline orvepitant maleate according to claim 1, further comprising X-ray powder diffraction pattern peaks at 10.7±0.1, 15.0±0.1, 15.3±0.1, 17.0±0.1, 17.5±0.1, 19.3±0.1, 19.6±0.1, 20.1±0.1, 20.3±0.1, 20.9±0.1, 21.1±0.1, 21.8 ±0.1, and 22.6±0.1 degrees 2 theta.

3. Anhydrous crystalline orvepitant maleate according to claim 2, further characterized by an X-ray powder diffraction pattern as depicted in FIG. 1.

4. Anhydrous crystalline orvepitant maleate according to claim 1, further characterized by $^{13}$C solid state nuclear magnetic resonance chemical shifts at 173.6±0.3, 172.6±0.3, 165.8±0.3, 164.0±0.3, 162.6±0.3, 160.1±0.3, 146.5±0.3, 140.4±0.3, 136.5±0.3, 132.4±0.3, 131.7±0.3, 129.3±0.3, 127.6±0.3, 126.5±0.3, 121.8±0.3, 114.7±0.3, 114.2±0.3, 64.6±0.3, 57.0±0.3, 56.5±0.3, 52.8±0.3, 51.2±0.3, 48.1±0.3, 43.7±0.3, 36.6±0.3, 30.2±0.3, 24.0±0.3, 22.9±0.3, 18.7±0.3, and 15.9±0.3 ppm.

5. Anhydrous crystalline orvepitant maleate according to claim 4, further characterized by a $^{13}$C solid state nuclear magnetic resonance spectrum as depicted in FIG. 3.

6. A pharmaceutical composition comprising anhydrous crystalline orvepitant maleate according to claim 1 and one or more pharmaceutically acceptable carriers or diluents.

7. A method for the treatment of a disorder selected from depression, anxiety, post traumatic stress disorder, emesis, and sleep disorder comprising administering to a mammal, an effective amount of anhydrous crystalline orvepitant maleate according to claim 1.

* * * * *